(12) United States Patent
Graham

(10) Patent No.: US 7,059,231 B2
(45) Date of Patent: Jun. 13, 2006

(54) DENTAL MODEL CUTTER

(76) Inventor: Neil John Graham, 6017 Lido La., Long Beach, CA (US) 90803

( * ) Notice: Subject to any disclaimer, the term of this patent is extended or adjusted under 35 U.S.C. 154(b) by 192 days.

(21) Appl. No.: 10/440,215

(22) Filed: May 19, 2003

(65) Prior Publication Data
US 2004/0231484 A1    Nov. 25, 2004

(51) Int. Cl.
    *B26D 7/02*    (2006.01)
(52) U.S. Cl. .............. 83/764; 83/452; 83/454; 83/464; 83/465; 83/762
(58) Field of Classification Search ........... 83/452, 83/454, 455, 464, 465, 468.2, 761, 762, 763, 83/764; 269/295; D7/673
    See application file for complete search history.

(56) References Cited

U.S. PATENT DOCUMENTS

| | | | | |
|---|---|---|---|---|
| 360,946 A | * | 4/1887 | Beekman | .............. 83/454 |
| 528,968 A | * | 11/1894 | Peabody | .............. 269/145 |
| 2,608,747 A | * | 9/1952 | Gamboney | .............. 83/454 |
| 3,583,026 A | * | 6/1971 | Peoni | .............. 452/16 |
| 3,971,273 A | * | 7/1976 | Peters et al. | .............. 83/762 X |
| 4,249,445 A | * | 2/1981 | Browning | .............. 83/762 |
| 4,399,989 A | * | 8/1983 | Baillie | .............. 83/762 X |
| D315,275 S | * | 3/1991 | Aziz et al. | .............. D7/673 |
| 5,361,666 A | * | 11/1994 | Kensrue | .............. 83/762 X |
| 5,724,877 A | * | 3/1998 | Kensrue | .............. 83/465 X |
| 6,286,405 B1 | * | 9/2001 | Hamm | .............. 269/295 X |
| 6,591,724 B1 | * | 7/2003 | Huang | .............. 83/464 X |

FOREIGN PATENT DOCUMENTS

JP    57-134222    *   8/1982    .............. 83/454

* cited by examiner

*Primary Examiner*—Clark F. Dexter
(74) *Attorney, Agent, or Firm*—Neil John Graham

(57) ABSTRACT

The invention is a dental model cutter for trimming the base of a dental model in a precise predetermined manner where the dental model is precisely secured and positioned under a cutting guide and can be hand sawed or cut, thus eliminating the need of a conventional dental model grinder.

12 Claims, 7 Drawing Sheets

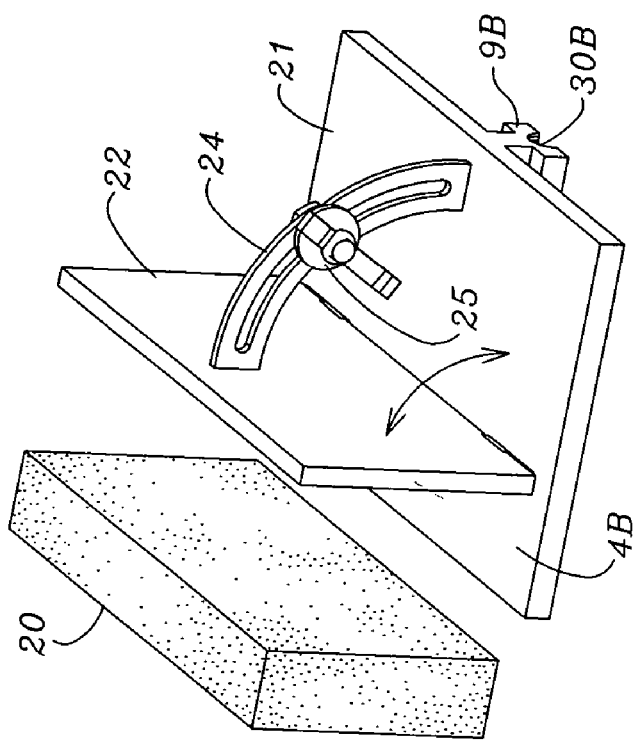
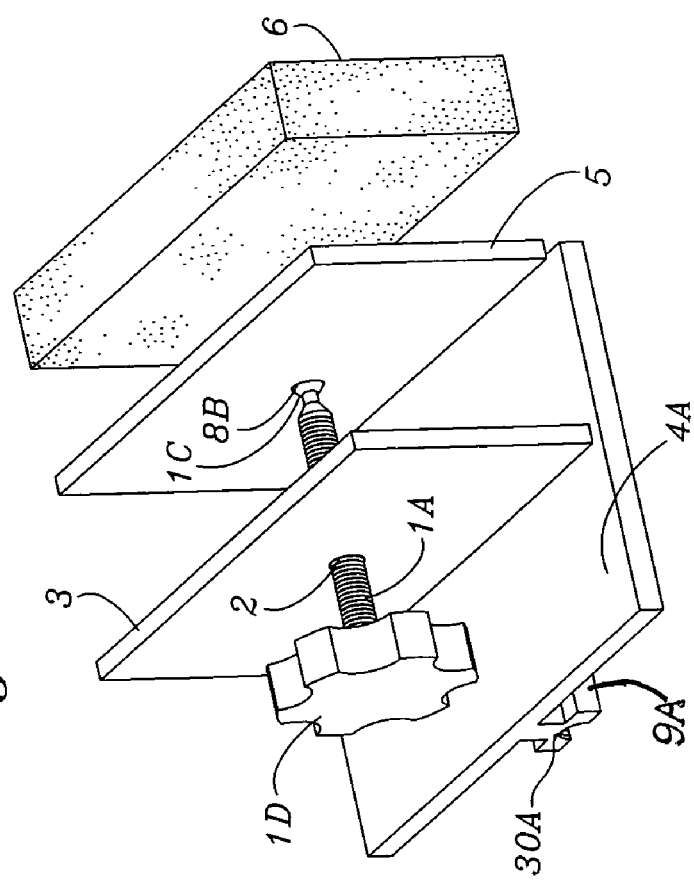

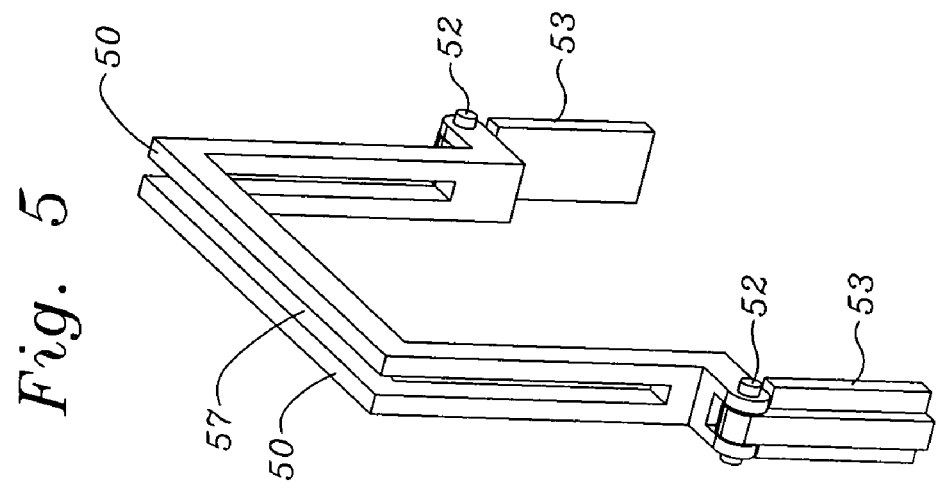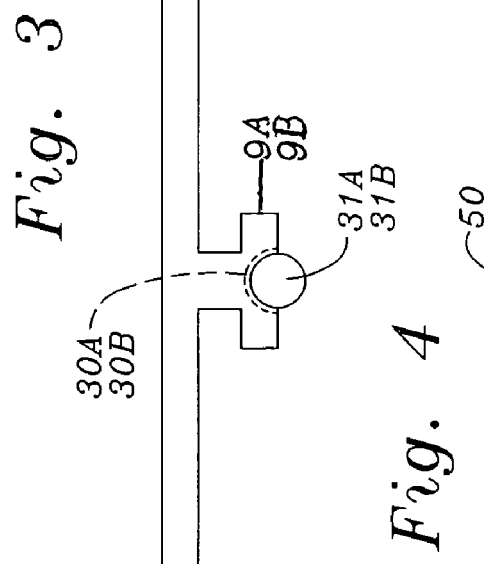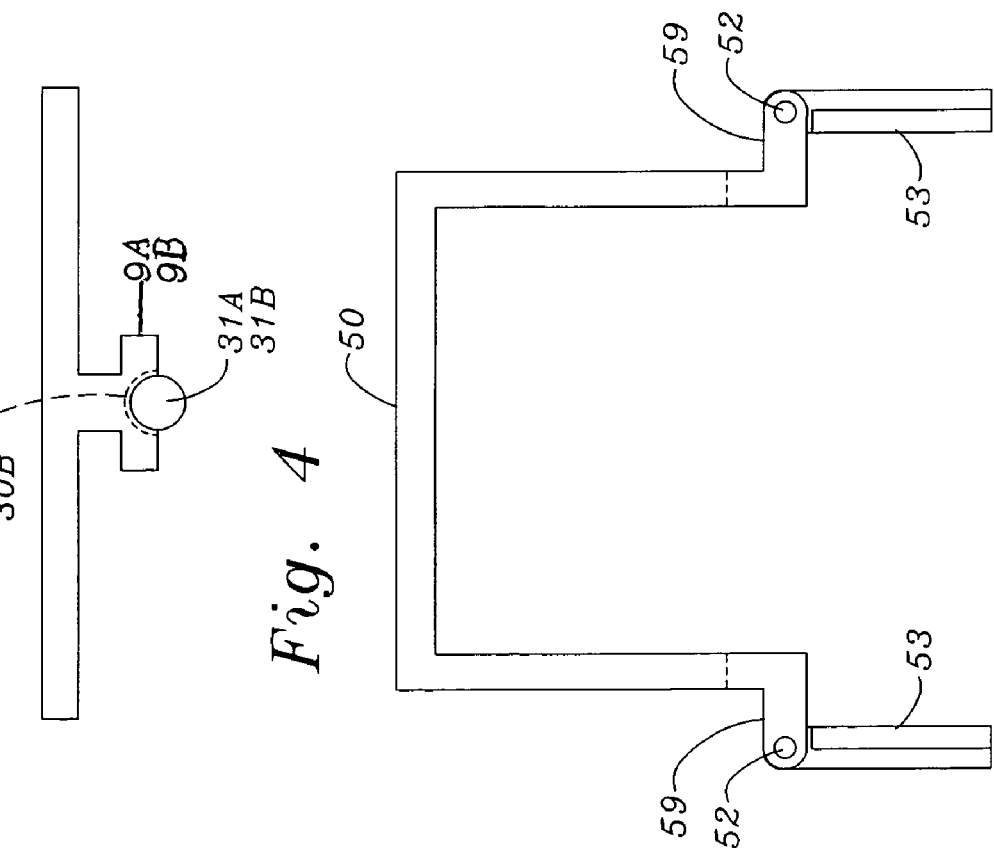

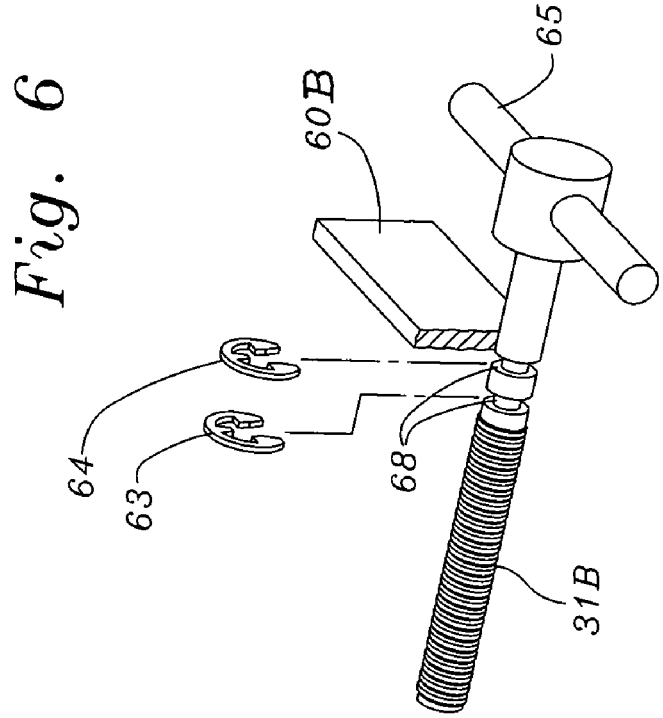
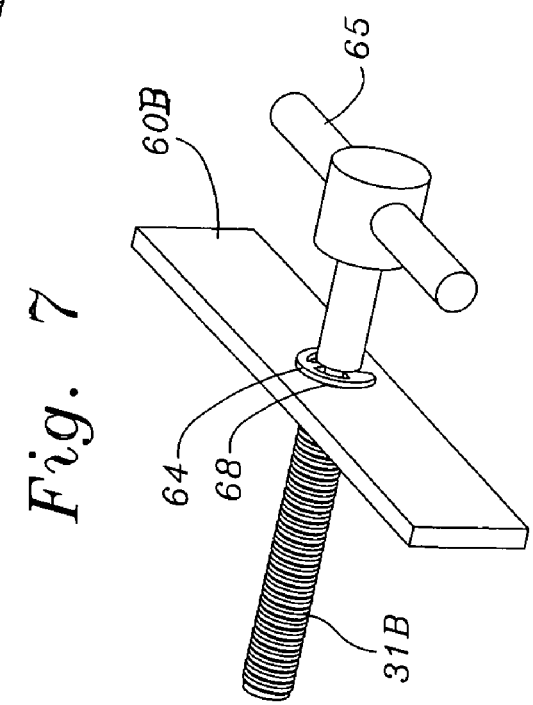
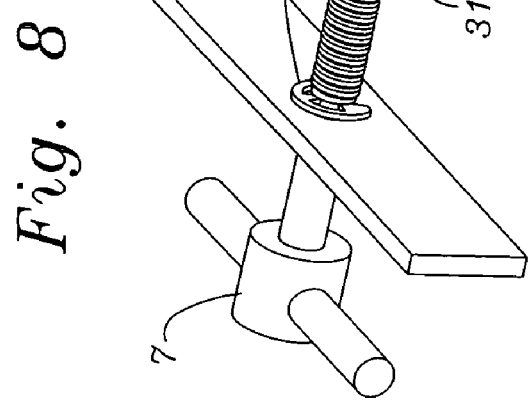

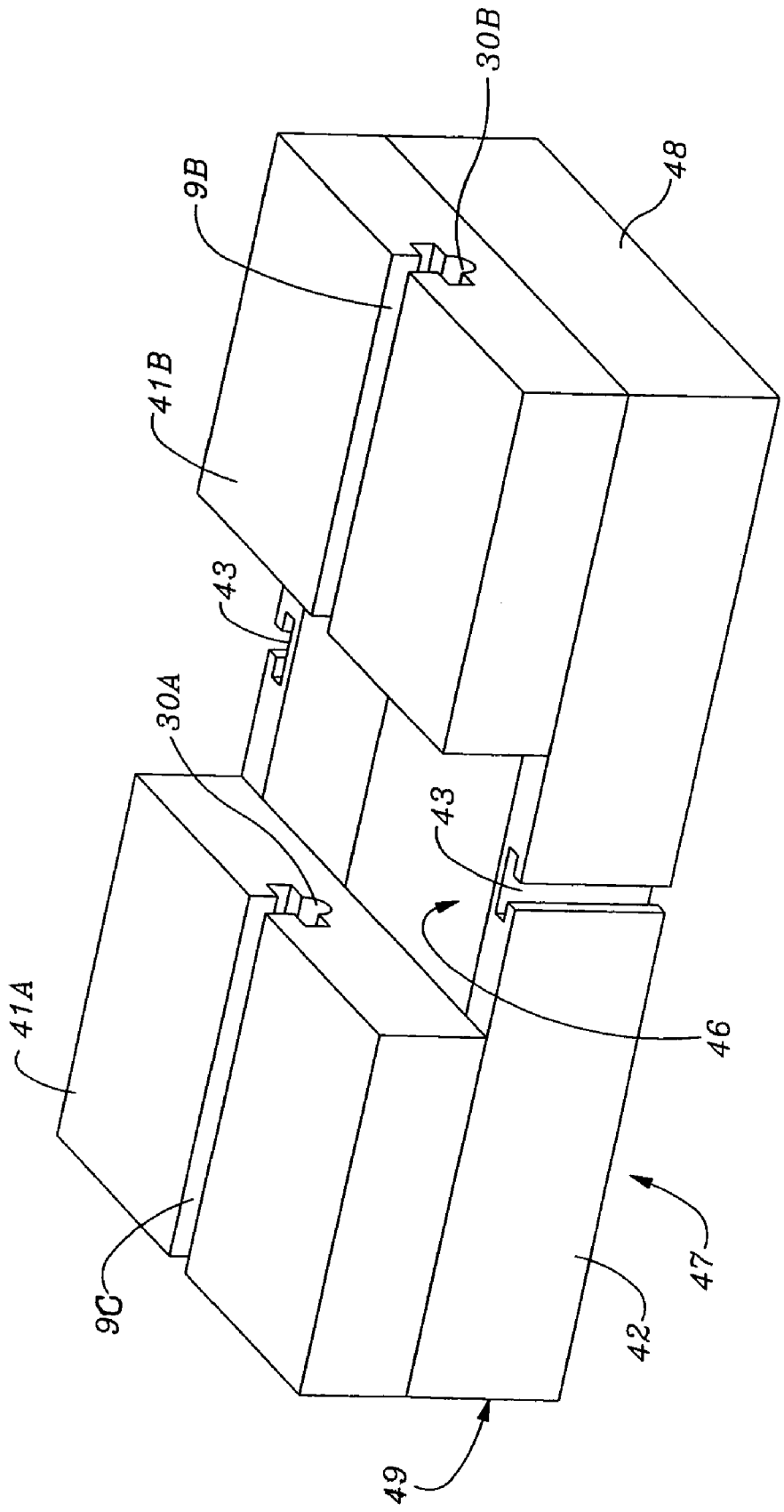

DENTAL MODEL CUTTER

FIELD OF INVENTION

The present invention is directed to a dental model trimming device for precisely cutting the base of a dental model without the creation of model dust, thus eliminating the requirement of running water with drainage or a high volume vacuum.

BACKGROUND OF THE INVENTION

Dental models are made of a patient's teeth for such reasons as: the construction of crowns, partial dentures, retainers, removable orthodontic appliances, and study models. Dental stone or plaster is poured into an impression of the patient's teeth which then hardens. The hardened model then has to be trimmed for its variety of uses. The model trimming is done with a machine called a model trimmer which consists of a motor powered flat abrasive wheel flushed with running water to remove the grindings. The grindings are flushed into a drain which requires a plaster trap to preventing blockage of the drain lines. The water also has the disadvantage of removing a slight amount of the model surface which decreases the model accuracy.

SUMMARY OF THE INVENTION

The present invention is directed towards a dental model cutter which allows a dental model to be precisely trimmed without the need of a conventional model trimmer, running water, any kind of drainage system, or a high powered air vacuum system. The dental model cutter holds a dental model in a firm position in relation to a slot guide for a hand or power saw which cuts the dental model.

The model cutter is comprised of a rectangular box approximately 6"×12" with ½" thick walls. The rectangular box has opposing vertical sides and opposing vertical longitudinal ends. The bottom of the box is open and the middle ⅓ of the upper part of the box is open. The remaining two thirds of the upper part of the box is covered with left and right 1" thick horizontal plates, each plate with an upper central T-slot groove which runs in the direction of the length of the box and is open to the top of the horizontal plate. A left and right horizontal sliding plate ½ thick sits upon the respective upper surface of each horizontal plate, each containing a male T-track extending from its lower side which runs in the same direction and fits within the female T-slot of the respective left and right horizontal T-slot, allowing the horizontal sliding plates to move to back and forth on the horizontal plates. A horizontal screw within each horizontal plate engages the lower part of each male T-track which is each threaded to fit its respective screw, rotation of the screws move the sliding plates back and forth on the horizontal plates. A left and right vertical metal plate, each with a cushion pad facing the open area of the box is adhered to each sliding plate for securing the dental model. A vertical C-shaped saw guide is mounted centrally to the longitudinal sides of the rectangular box to guide a means for cutting the dental model, such as a hand saw. The dental model is positioned between the left and right vertical plates and the sliding plates are moved using the horizontal screws until the dental model is positioned appropriately below the cutting guide wherein the dental model is then cut.

In one embodiment of the present invention a horizontal adjustable handle is mounted to the center of the left vertical plate with the handle to the left. The shaft of the handle passes through the vertical plate and is attached with a ball socket joined to a second free vertical plate with a foam pad on the opposite side. The movement of the free vertical plate enhances the fit to an irregular model base. The adjustable handle provides a quicker more finite method of adjusting the tension on the model and provides an easy method of clamping to successive dental models without adjustment of the sliding plates.

In another embodiment of the invention the right vertical plate is hinged to the sliding plate and has an adjustment bar for altering the position of the model allowing for a more precise cut of the dental model.

BRIEF DESCRIPTION OF DRAWINGS

FIG. 1 is a perspective view of the left sliding plate;
FIG. 2 is a perspective view of the right sliding plate;
FIG. 3 is an end view of a sliding plate;
FIG. 4 is an end view of the vertical saw guide;
FIG. 5 is a perspective view of the vertical saw guide;
FIG. 6 is a perspective view of the right end plate with right horizontal screw, C-clamps, and handle;
FIG. 7 is a perspective exploded view of the horizontal screw handle;
FIG. 8 is a perspective view of the left end plate and left horizontal screw with handle;
FIG. 9 is a perspective view of the rectangular box with left and right horizontal plates.

DETAILED DESCRIPTION OF THE INVENTION

Figure 10:
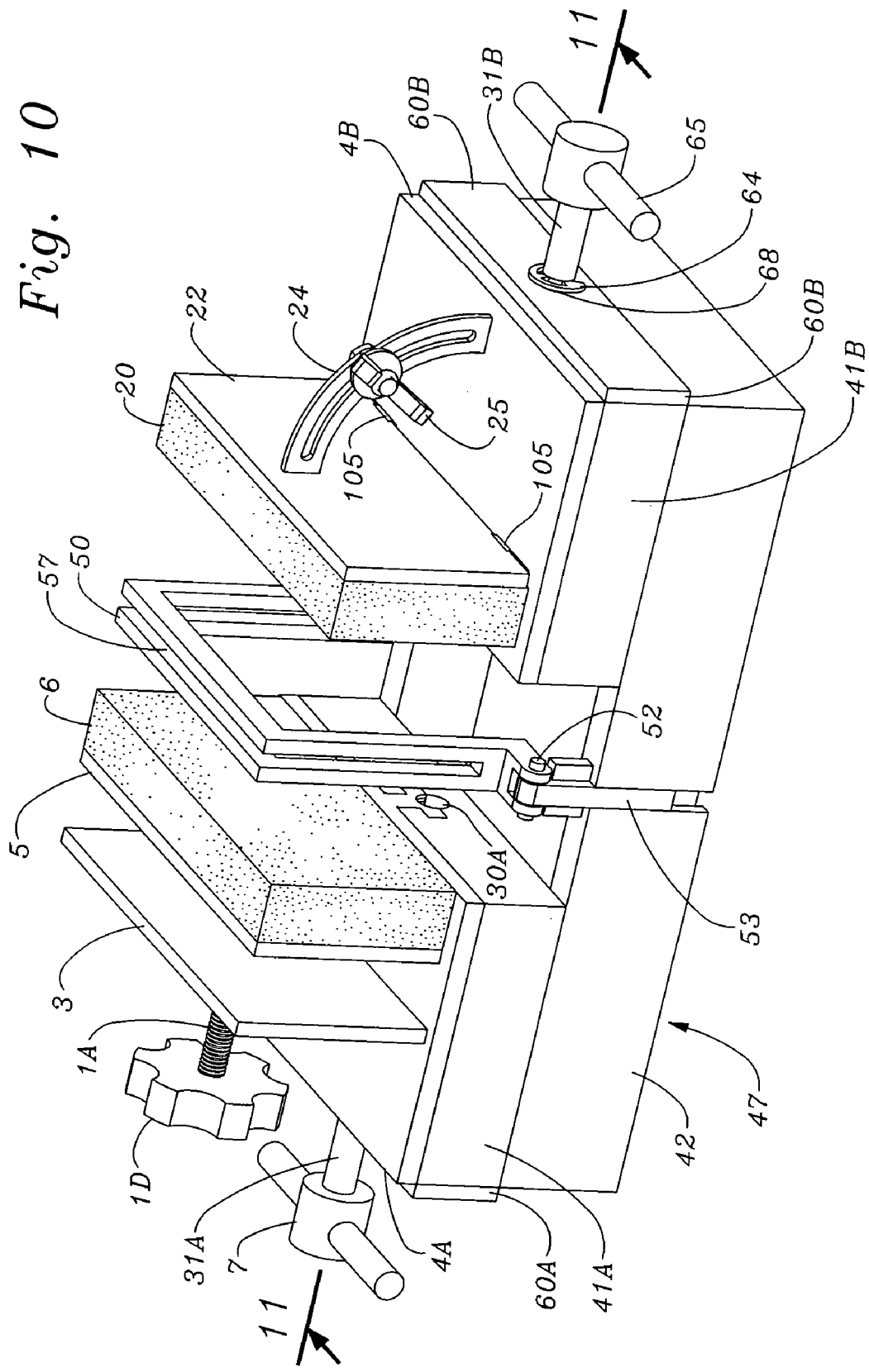
FIG. 10 is a perspective view of the dental model cutter on a box base.
Figure 11:
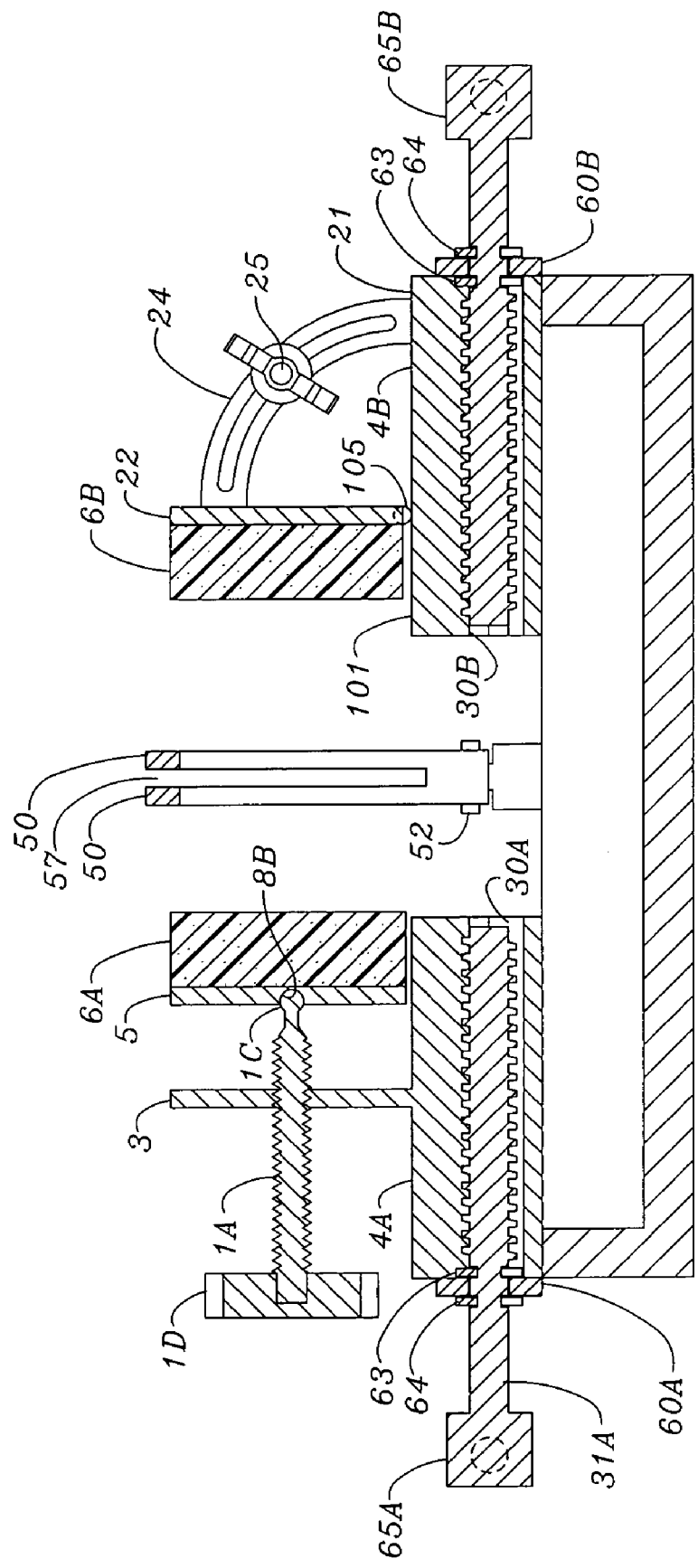
FIG. 11 is a side cross-sectional view of the dental model cutter through the longitudinal center.

The dental model cutter is comprised of an adjustable model holder, as in FIGS. 1 and 2, mounted on a longitudinal rectangular box 42 as a base, as shown in FIGS. 9 and 10. The outer dimension of the rectangular box is 6"×12". The walls of the rectangular box 42 are composed of opposing sides and opposing longitudinal right end 48 and left end 49. The walls of the rectangular box are ½" thick and 1" high. The rectangular box 42 has an open top 46 and an open bottom 47. Attached horizontally to the top 46 of the rectangular box 42 are a left horizontal plate 41A and a right horizontal plate 41B, one at each end of the rectangular box 42 and each 6"×4"×1", the 4" dimension in the same longitudinal direction as the rectangular box 42. As shown in FIG. 9, with the left horizontal plate 41A and the right horizontal plate 41B attached to the top 46 of the rectangular box 42 the rectangular box has an open upper center between the left horizontal plate 41A and right horizontal 41B. In FIG. 9 on the upper surface of the left horizontal plate 41A is a left central female T-slot 9A and in the right horizontal 41B is a right central female T-slot 9B in the longitudinal direction of the length of the rectangular box 42. Referring to FIGS. 10 and 11 a left horizontal male screw 31A is enclosed within a left cylindrical longitudinal bore 30C and a right horizontal male screw 31B is enclosed within a right cylindrical longitudinal bore 30D. It is important the left cylindrical longitudinal bore 30A and the right longitudinal bore 30B are not threaded which assures the left horizontal male screw 31A stays in the same position in the left cylindrical longitudinal bore 30C and the right horizontal male screw 31B stays in the same position within the right cylindrical longitudinal bore 30D. In FIG. 9 the upper part of the left cylindrical longitudinal bore 30C is open to lower part of the left central female T-slot 9A and the upper part of the right cylindrical longitudinal bore 30D is open to the lower part of the right central female T-slot FIG. 9B.

Referring to FIGS. 1, 2, 3, 10, 11 and 12 the dental model cutter has a left sliding plate 4A and a right sliding plate 4B, each 4"×6", the 4" dimension in the longitudinal axis of the rectangular box 42. The left and right sliding plates 4A and 4B each have a longitudinal axis the same as the rectangular box 42. The left sliding plate 4A sits horizontally on top of the left horizontal plate 41A and the right sliding plate 4B sits horizontally on the top of the right horizontal plate 41B and each have the same rectangular dimension as the horizontal plates 41A and 41B and are ⅛" thick. Referring to FIGS. 1, 2 and 3 a left male T-track 10A is integral and runs longitudinal in the center of the lower part of the left horizontal sliding plate 4A and a right male T-track 10B runs longitudinally in the center of the lower part of the right horizontal sliding plate 4B. Referring to FIG. 3 the lower surface 30A of the left male T-track 10A and the lower surface 30B of the right male T-track are grooved and threaded to match the threads of the left horizontal screw 31A and the right horizontal screw 31B. The left horizontal sliding plate 4A is attached to the left horizontal plate 41A by placing the left male T-track 10A into the left central female T-slot 9A and the right horizontal sliding plate 4B is attached to the right horizontal plate 41B by placing the right male T-track 10B into the right central female T-slot 9B. The left horizontal screw 31A is placed within the left horizontal bore 30C wherein the left horizontal screw 31A engages the threaded portion 30A of the left male T-track 10A. The right horizontal screw 31B is placed within the right horizontal bore 30D wherein the right horizontal screw 31B engages the threaded portion 30B of the right male T-track 10B. The right sliding plate 4B is assembled with the right horizontal screw 31B and right horizontal plate 41B. In FIGS. 6,7,8, and 10 a left end plate 60A with an inner and outer surface is attached to the outer longitudinal end of the left horizontal plate 41A to secure the horizontal position of the left horizontal male screw 31A and a right end plate 60B with an inner and outer surface is attached to the outer longitudinal end of the right horizontal plate 41B to secure and maintain the horizontal position of the right horizontal screw 31B. In FIGS. 6 and 7 the left and right horizontal screws 31A and 31B each have circumferential grooves 68 corresponding to the inner and outer surfaces of the respective left end plate 60A and the right end plate 60B. Inside C-clamps 63 and outside C-clamps 64 are placed in the circumferential grooves 68 which secure the left horizontal screw 31A and the right horizontal screw 31B in their horizontal positions wherein turning of the left horizontal screw 31A with the left handle 65A moves the left sliding plate 4A and turning of the right horizontal screw 31B with the right handle 65B moves the right sliding plate 4B In FIGS. 1 and 12 a left vertical plate 3 is mounted to the upper surface of the left horizontal sliding plate 4A 1" from the left end of the left horizontal sliding plate 4A at a right angle to the longitudinal axis of the dental model cutter. The left vertical plate 3 is ⅛" thick, 4" in width and 4" tall. In an embodiment of the dental model cutter, FIGS. 11 and 12, a left free vertical plate 3 is positioned ¾ from the right horizontal end of the left sliding plate 4A wherein a left cushion pad 6 is placed on the right flat surface of the left free vertical plate 5 placing the flat open surface of the left cushion pad 6 at the right longitudinal end of the left horizontal sliding plate 4A. In FIG. 1 the center of the left vertical plate 3 has a threaded hole 2 in its center which receives a 4" long adjustable screw 1A with a handle 1D mounted at the left end and a ball 1C at the right end. The adjustable screw 1A attaches to the left vertical plate 3 threaded center hole 2, extends horizontally where its ball end 1C fits into a socket 8B in the center of a the free vertical plate 5 which is the same dimension as the left vertical plate 3. In FIG. 10 the free vertical plate 5 is ¾" from the right longitudinal end of the left sliding plate 4A and the cushion pad 6 is attached to the right surface of the free vertical plate 5 which places the free surface of the left cushion pad 6 even with the right end of the left sliding plate 4A.

Figure 12:
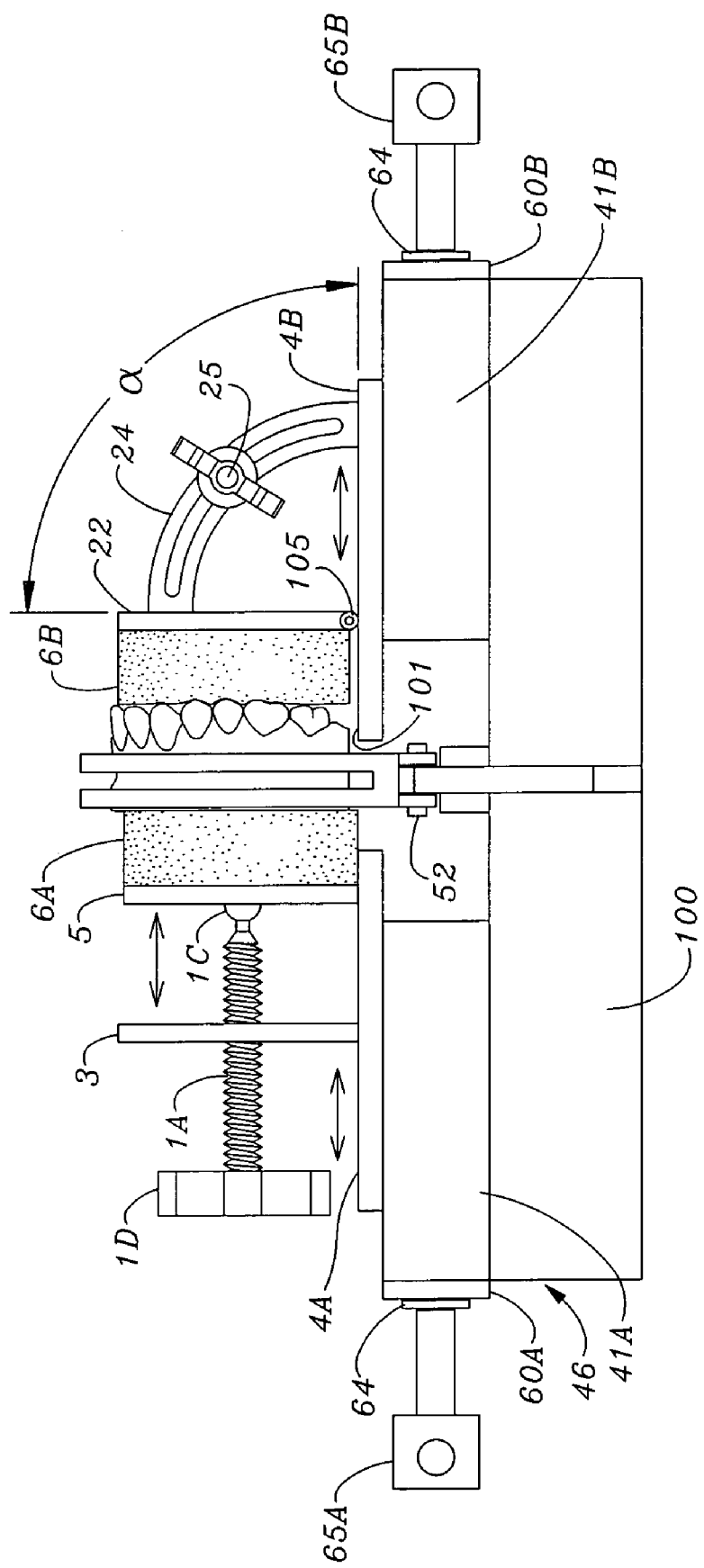
FIG. 12 is a side view of the dental model cutter with a mounted dental model.

In FIGS. 2,10,11 and 12 a right vertical plate 22 is mounted to the top of the right sliding plate 4B 1" from the left longitudinal end, a right cushion pad 20 is attached on the open flat surface of the right vertical plate 22. As shown in FIGS. 10, 11 and 12 the right cushion pad 20 has a thickness as such that leaves a 4–8 mm. of the right horizontal sliding plate 4A open at its left top surface to allow the heel of a dental model to sit on the right sliding plate 4A top surface 21.

In another embodiment of the invention, FIGS. 2,9,10 and 11, the right vertical plate 22, 4"×6"×⅛", is swivel mounted 105 to the upper surface 21 of the right sliding plate 4B ¾" from the left end the right sliding plate 4B allowing an open surface on the right sliding plate 4B top surface for the heal of the dental model to vertically rest as shown in FIG. 12. An adjustable arm 24 is mounted from the upper center, right, surface of the right vertical plate 22 to the upper surface of the right sliding plate 4B. The adjustment arm 24 is comprised of two pieces, one sliding over the other with a locking nut and bolt 25 which locks the adjustable arm 24 in a chosen position. The adjustable arm 24 allows the vertical angle of the right vertical plate 22 to be changed which affects the cut of the dental model in relation to the position of the teeth. In FIGS. 10, 11 and 12 the right cushion pad 20, ½"×4"×4", is adhesively attached to the left surface of the right vertical plate 22.

In FIGS. 4,5 and 9 the dental model cutter also has a vertical C-shaped saw guide 50 fitted centrally in the rectangular box 42 comprising lower T-shaped male ends 53 which are fitted into vertical T-slots 43 located in the center of the opposing sides of the rectangular box 42. Each male T-shaped end 53 is connected by a pivoting pin 52 to a 1" first end of a horizontal section 59 of the saw guide 50. The horizontal section 59 is solid and ½" wide and has a second inner end. Attached to the inner end of each horizontal section 59 is a vertical C-shaped saw guide 50 which extends 4" vertically and 4" across the top. The vertical C-shaped guide 50 has a center slot 57 2–4 mm. wide to allow for a saw blade width. It is important the horizontal width of the C-shaped saw guide is 4" which allows for the back and forth sawing motion of a short-bladed saw such as a jeweler's saw.

The invention has been discussed with specific embodiments. The purpose of the dental model cutter is to provide a way to trim the base of a dental model by cutting the model, not grinding it. The model cutter holds the model precisely in relation to a cutting guide. The cutting means is not intended to be limited to a saw blade; the invention is intended to include any means that would cut a dental model.

What is claimed:

1. A dental model cutting device for precision cutting the base of a dental model comprising:
   a base having a horizontal longitudinal axis with opposing left and right longitudinal ends, opposing sides with centers, a vertical T-track in the center of each side and a top and a bottom wherein the top and bottom are open;
   a left horizontal plate with left and right ends, opposing sides and a top and a bottom, the top having a center containing a central female T-slot and a left horizontal bore with a diameter, left and right ends and an open top, the female T-slot above the left horizontal bore and connecting with the left horizontal bore open top, wherein the bottom of the left horizontal plate is mounted on the left top of the base with the central female T-slot and horizontal bore in the same longitudinal axis as the base;

a right horizontal plate with left and right ends, opposing sides and a top and a bottom, the top having a center containing a central female T-slot and a right horizontal bore with a diameter, left and right ends and an open top, the female T-slot above the right horizontal bore and connecting with the right horizontal bore, wherein the bottom of the right horizontal plate is mounted on the right top of the base with the central female T-slot and horizontal bore in the same longitudinal axis as the base;

a left horizontal sliding plate with left and right ends, opposing sides and a top and a bottom, the bottom having a center containing a central male T-track with a bottom with a horizontal arcuate threaded groove wherein the bottom of the left horizontal sliding plate is mounted on the top of the left horizontal plate with the central male T-track mounted within the central female T-slot of the left horizontal plate with the horizontal arcuate groove connecting to the open top of the horizontal bore of the left horizontal plate;

a right horizontal sliding plate with left and right ends, opposing sides and a top and a bottom, the bottom having a center containing a central male T-track with a bottom with a horizontal arcuate threaded groove wherein the bottom of the right horizontal sliding plate is mounted on the top of the right horizontal plate with the central male T-track mounted within the central female T-slot of the right horizontal plate with the horizontal arcuate threaded groove connecting to the open top of the horizontal bore of the right horizontal plate;

a left vertical plate with a top, bottom, sides and left and right flat surfaces vertically mounted by the left vertical plate bottom to the top of the left horizontal sliding plate near the right end of the left horizontal plate;

a right vertical plate with a top, a bottom, left and right flat surfaces, attached at the bottom to the top of the right sliding plate near the left end of the right sliding plate;

left and right cushion pads with left and right flat surfaces, the left cushion pad attached by its left flat surface to the right flat surface of the left vertical plate and the right cushion pad attached by its right flat surface to the left flat surface of the right vertical plate;

a left end plate with opposing sides and a central hole with a diameter wherein the left end plate is mounted to the left end of the left horizontal plate with the central hole aligned with left horizontal plate horizontal bore, the central hole with the same diameter as the left horizontal bore;

a right end plate with opposing sides and a central hole with a diameter wherein the right end plate is mounted to the right end of the right horizontal plate with the central hole aligned with right horizontal plate horizontal bore, the central hole with the same diameter as the right horizontal bore;

a threaded left horizontal screw with left and right ends and a diameter slightly smaller than the left horizontal bore diameter, a handle mounted on the left end of the left threaded horizontal screw and two circumferential grooves near the left end of the left horizontal screw wherein when the right end of the left horizontal screw is placed into the left end of the left horizontal bore, two C-clamps are placed in the left horizontal screw circumferential grooves, one on each opposing side of the left end plate, securing the left horizontal screw within the bore of the left horizontal plate securing the left threaded horizontal screw within the horizontal bore of the left horizontal plate and the left horizontal screw engages the threaded bottom groove of the bottom of the male T-track of the left sliding plate and the threaded left horizontal screw engages with the threaded bottom groove of the bottom of the male T-track of the left sliding plate;

a threaded right horizontal screw with left and right ends and a diameter slightly smaller than the right horizontal bore diameter, a handle mounted on the right end and two circumferential grooves near the right end of the right horizontal screw wherein when the left end of the right horizontal screw is placed within the right end of the right horizontal bore two C-clamps are placed in the circumferential grooves, one on each side of the right end plate, securing the right threaded horizontal screw within the horizontal bore of the right horizontal plate and the threaded right horizontal screw engages the threaded bottom groove of the bottom of the male T-track of the right sliding plate and the threaded right horizontal screw engages with the threaded bottom groove of the bottom of the male T-track of the right sliding plate; and a vertical C-shaped slotted cutting guide with a top, a bottom with pivot pins, two vertical male T-tracks attached to the pivot pins wherein the vertical male T-tracks are inserted into the vertical female T-slots in the sides of the base whereby a dental model is precisely secured and positioned under the C-shaped cutting guide by placing a dental model on the left flat surface of the right cushion pad and turning the right horizontal screw counterclockwise which turns the right horizontal screw counterclockwise within the right horizontal bore, the right horizontal screw engaging the threads of the right male threaded T-slot which advances the right horizontal sliding plate with the attached right cushion pad and the dental model towards the dental model's desired position under the C-shaped cutting guide wherein the left horizontal screw handle is turned counterclockwise which advances the left horizontal sliding plate with the left cushion pad towards the dental model until the right flat surface of the left cushion pad engages the dental model and the dental model is held firmly between the left and right cushion pads.

2. A dental model cutting device as in claim 1 wherein the base is rectangular and 6"×12".

3. A dental model cutting device as in claim 1 wherein the sliding plates are 6"×4"×¼", the 4" dimension is along the horizontal longitudinal axis of said base.

4. A dental model cutting device as in claim 1 wherein the vertical plates are 6" wide, 4" tall, and ⅛" thick.

5. A dental model cutting device for precision cutting the base of a dental model comprising:

a base having a horizontal longitudinal axis with opposing left and right longitudinal ends, opposing sides with centers, a vertical T-track in the center of each side and a top and a bottom wherein the top and bottom are open;

a left horizontal plate with left and right ends, opposing sides and a top and a bottom, the top having a center containing a central female T-slot and a left horizontal bore with left and right ends and an open top, the female T-slot above the left horizontal bore and connecting with the left horizontal bore open top, wherein the bottom of the left horizontal plate is mounted on the left top of the base with the central female T-slot and horizontal bore in the same longitudinal axis as the base;

a right horizontal plate with left and right ends, opposing sides and a top and a bottom, the top having a center containing a central female T-slot and a horizontal bore with left and right ends, the female T-slot above the right horizontal bore and connecting with the right horizontal bore, wherein the bottom of the right horizontal plate is mounted on the right top of the base with the central female T-slot and horizontal bore in the same longitudinal axis as the base;

a left horizontal sliding plate with left and right ends, opposing sides and a top and a bottom, the bottom having a center containing a central male T-track with a bottom with a horizontal arcuate threaded groove wherein the bottom of the left horizontal sliding plate is mounted on the top of the left horizontal plate with the central male T-track mounted within the central female T-slot of the left horizontal plate with the horizontal arcuate groove connecting to the open top of the horizontal bore of the left horizontal plate;

a right horizontal sliding plate with left and right ends, opposing sides and a top and a bottom, the bottom having a center containing a central male T-track with a bottom with a horizontal arcuate threaded groove wherein the bottom of the right horizontal sliding plate is mounted on the top of the right horizontal plate with the central male T-track mounted within the central female T-slot of the right horizontal plate with the horizontal arcuate threaded groove connecting to the open top of the horizontal bore of the right horizontal plate;

a left vertical plate with a top, bottom, sides and left and right flat surfaces vertically mounted by the left vertical plate bottom to the top of the left horizontal sliding plate near the right end of the left horizontal plate;

a right vertical plate with a top, a bottom, left and right flat surfaces, hinges attached to the bottom and an adjustable arm with left and right ends, the left end attached to the right flat surface of the right vertical plate wherein the right vertical plate bottom is vertically mounted with the hinges to the top of the right horizontal sliding plate between the opposing right sliding plate sides and midway between the right sliding plate left and right ends, and the adjustable arm right end is attached to the top surface of the right sliding plate;

left and right cushion pads, the left cushion pad attached to the right flat surface of the left vertical plate and the right cushion pad attached to the left flat surface of the right vertical plate;

a left end plate with a central hole with a diameter wherein the left end plate is mounted to the left end of the left horizontal plate with the central hole aligned with left horizontal plate horizontal bore, the central hole the same diameter as the left horizontal bore;

a right end plate with a central hole with a diameter wherein the right end plate is mounted to the right end of the right horizontal plate with the central hole aligned with right horizontal plate horizontal bore, the central hole the same diameter as the right horizontal bore;

a threaded left horizontal screw with left and right ends and a diameter slightly smaller than the left horizontal bore diameter, a handle mounted on the left end of the left threaded horizontal screw and two circumferential grooves near the left end of the left horizontal screw wherein when the right end of the left horizontal screw is placed into the left end of the left horizontal bore, two C-clamps are placed in the left horizontal screw circumferential grooves, one on each side of the left end plate, securing the left horizontal screw within the bore of the left horizontal plate, securing the left threaded horizontal screw within the horizontal bore of the left horizontal plate and the left horizontal screw engages the threaded bottom groove of the bottom of the male T-track of the left sliding plate;

a threaded right horizontal screw with left and right ends and a diameter slightly smaller than the right horizontal bore diameter, a handle mounted on the right end and two circumferential grooves near the right end of the right horizontal screw wherein when the left end of the right horizontal screw is placed within the right end of the right horizontal bore two C-clamps are placed in the circumferential grooves, one on each side of the right end plate, securing the right threaded horizontal screw within the horizontal bore of the right horizontal plate and the threaded right horizontal screw engages the threaded bottom groove of the bottom of the male T-track of the right sliding plate; and a vertical C-shaped slotted cutting guide with a top, a bottom with pivot pins, two vertical male T-tracks attached to the pivot pins wherein the vertical male T-tracks are inserted into the vertical female T-slots in the sides of the base whereby a dental model is precisely secured and positioned under the C-shaped cutting guide by placing a dental model on the left flat surface of the right cushion pad, adjusting the adjustable arm of the right vertical plate to attain a desired tilt of the dental model, and turning the right horizontal screw counterclockwise which turns the right horizontal screw counterclockwise within the right horizontal bore, the right horizontal screw engaging the threads of the right male threaded T-slot which advances the right horizontal sliding plate with the attached right cushion pad and the dental model towards the dental model's desired position under the C-shaped cutting guide wherein the left horizontal screw handle is turned counterclockwise which advances the left horizontal sliding plate with the left cushion pad towards the dental model until the right flat surface of the left cushion pad engages the dental model and the dental model is held firmly between the left and right cushion pads.

6. A dental model cutting device as in claim 5 wherein the base is rectangular and 6"×12".

7. A dental model cutting device as in claim 5 wherein the sliding plates are 6"×4" by ¼" thick.

8. A dental model cutting device as in claim 5 wherein the vertical plates are 6" wide, 4" tall, and ⅛" thick.

9. A dental model cutting device for precision cutting the base of a dental model comprising:

a base having a horizontal longitudinal axis with opposing left and right longitudinal ends, opposing with centers, a vertical T-track in the center of each side and a top and a bottom wherein the top and bottom are open;

a left horizontal plate with left and right ends, opposing sides and a top and a bottom, the top having a center containing a central female T-slot and a left horizontal bore with left and right ends and an open top, the female T-slot above the left horizontal bore and connecting with the left horizontal bore open top, wherein the bottom of the left horizontal plate is mounted on the left top of the base with the central female T-slot and horizontal bore in the same longitudinal axis as the base;

a right horizontal plate with left and right ends, opposing sides and a top and a bottom, the top having a center containing a central female T-slot and a horizontal bore with left and right ends, the female T-slot above the right horizontal bore and connecting with the right horizontal bore, wherein the bottom of the right horizontal plate is mounted on the right top of the base with the central female T-slot and horizontal bore in the same longitudinal axis as the base;

a left horizontal sliding plate with left and right ends, opposing sides and a top and a bottom, the bottom having a center containing a central male T-track with a bottom with a horizontal arcuate threaded groove wherein the bottom of the left horizontal sliding plate is mounted on the top of the left horizontal plate with the central male T-track mounted within the central female T-slot of the left horizontal plate with the horizontal arcuate groove connecting to the open top of the horizontal bore of the left horizontal plate;

a right horizontal sliding plate with left and right ends, opposing sides and a top and a bottom, the bottom having a center containing a central male T-track with a bottom with a horizontal arcuate threaded groove wherein the bottom of the right horizontal sliding plate is mounted on the top of the right horizontal plate with the central male T-track mounted within the central female T-slot of the right horizontal plate with the horizontal arcuate threaded groove connecting to the open top of the horizontal bore of the right horizontal plate;

a left vertical plate with a top, bottom, sides and left and right flat surfaces with a center defining a threaded hole wherein the left vertical plate is vertically mounted by the left vertical plate bottom to the top of the left horizontal sliding plate between the opposing left sliding plate sides and midway between the left sliding plate left and right ends;

a threaded adjustable screw with a left end, a center, a right end, a handle mounted to the left end and a ball at the right end;

a left free vertical plate with a top, bottom, left flat surface, right flat surface and a center of the flat surfaces containing a spherical socket sized to fit the ball of the adjustable screw wherein the left free vertical plate is mounted to the threaded adjustable screw by the insertion of the ball of the adjustable screw into the socket of the left free vertical plate;

a right vertical plate with a top, a bottom, left and right flat surfaces, hinges attached to the bottom and an adjustable arm with left and right ends, the left end attached to the right flat surface of the right vertical plate wherein the right vertical plate bottom is vertically mounted with the hinges to the top of the right horizontal sliding plate between the opposing right sliding plate sides and midway between the right sliding plate left and right ends and the adjustable arm right end is attached to the top surface of the right sliding plate;

left and right cushion pads, the left cushion pad attached to the right flat surface of the left free vertical plate and the right cushion pad attached to the left flat surface of the right vertical plate;

a left end plate with a central hole with a diameter wherein the left end plate is mounted to the left end of the left horizontal plate with the central hole aligned with left horizontal plate horizontal bore, the central hole the same diameter as the left horizontal bore;

a right end plate with a central hole with a diameter wherein the right end plate is mounted to the right end of the right horizontal plate with the central hole aligned with right horizontal plate horizontal bore, the central hole the same diameter as the right horizontal bore;

a threaded left horizontal screw with left and right ends and a diameter slightly smaller than the left horizontal bore diameter, a handle mounted on the left end of the left threaded horizontal screw and two circumferential grooves near the left end of the left horizontal screw wherein when the right end of the left horizontal screw is placed into the left end of the left horizontal bore, two C-clamps are placed in the left horizontal screw circumferential grooves, one on each side of the left end plate, securing the left horizontal screw within the bore of the left horizontal plate, securing the left threaded horizontal screw within the horizontal bore of the left horizontal plate and the left horizontal screw engages the threaded bottom groove of the bottom of the male T-track of the left sliding plate;

a threaded right horizontal screw with left and right ends and a diameter slightly smaller than the right horizontal bore diameter, a handle mounted on the right end and two circumferential grooves near the right end of the right horizontal screw wherein when the left end of the right horizontal screw is placed within the right end of the right horizontal bore two C-clamps are placed in the circumferential grooves, one on each side of the right end plate, securing the right threaded horizontal screw within the horizontal bore of the right horizontal plate and the threaded right horizontal screw engages the threaded bottom groove of the bottom of the male T-track of the right sliding plate; and a vertical C-shaped slotted cutting guide with a top, a bottom with pivot pins, two vertical male T-tracks attached to the pivot pins wherein the vertical male T-tracks are inserted into the vertical female T-slots in the sides of the base whereby a dental model is precisely secured and positioned under the C-shaped cutting guide by placing a dental model on the left flat surface of the right cushion pad adjusting the adjustable arm of the right vertical plate to attain a desired tilt of the dental model and turning the right horizontal screw counterclockwise which turns the right horizontal screw counterclockwise within the right horizontal bore, the right horizontal screw engaging the threads of the right male threaded T-slot which advances the right horizontal sliding plate with the attached right cushion pad and the dental model towards the dental model's desired position under the C-shaped cutting guide wherein the left horizontal screw handle is turned counterclockwise which advances the left free vertical plate with the left cushion pad towards the dental model until the right flat surface of the left cushion pad engages the dental model and the dental model is held firmly between the left and right cushion pads.

10. A dental model cutting device as in claim 9 wherein the base is rectangular and 6"×12".

11. A dental model cutting device as in claim 9 wherein the sliding plates are 6"×4"×¼" thick.

12. A dental model cutting device as in claim 9 wherein the vertical plates are 6" wide, 4" tall, and ⅛" thick and the sliding plates are moved towards the axial longitudinal middle of the base where the vertical plates secure a vertically positioned dental model.

* * * * *